US011548843B2

(12) United States Patent
Reyneke

(10) Patent No.: US 11,548,843 B2
(45) Date of Patent: Jan. 10, 2023

(54) SYSTEM FOR RECOVERY OF PROPYLENE FROM A PROPANE DEHYDROGENATION PROCESS

(71) Applicant: Rian Reyneke, Katy, TX (US)

(72) Inventor: Rian Reyneke, Katy, TX (US)

(73) Assignee: Kellogg Brown & Root LLC, Houston, TX (US)

(\*) Notice: Subject to any disclaimer, the term of this patent is extended or adjusted under 35 U.S.C. 154(b) by 0 days.

(21) Appl. No.: 17/510,580

(22) Filed: Oct. 26, 2021

(65) Prior Publication Data

US 2022/0041528 A1 Feb. 10, 2022

Related U.S. Application Data

(62) Division of application No. 17/016,512, filed on Sep. 10, 2020, now Pat. No. 11,198,661.

(60) Provisional application No. 62/898,426, filed on Sep. 10, 2019.

(51) Int. Cl.
*B01D 3/32* (2006.01)
*C07C 7/00* (2006.01)
*C07C 7/09* (2006.01)
*B01D 5/00* (2006.01)
*C07C 7/04* (2006.01)

(52) U.S. Cl.
CPC ............ *C07C 7/005* (2013.01); *B01D 3/32* (2013.01); *B01D 5/0063* (2013.01); *C07C 7/04* (2013.01); *C07C 7/09* (2013.01)

(58) Field of Classification Search
None
See application file for complete search history.

(56) References Cited

U.S. PATENT DOCUMENTS

| | | | | |
|---|---|---|---|---|
| 4,121,917 A | * | 10/1978 | Baker | F25J 3/0242 62/50.2 |
| 4,167,402 A | * | 9/1979 | Davis | F25J 3/0233 62/935 |
| 2008/0081938 A1 | * | 4/2008 | Schultz | C07C 7/11 585/648 |
| 2017/0305814 A1 | * | 10/2017 | Arocha | C07C 5/333 |
| 2018/0265430 A1 | * | 9/2018 | Kim | B01D 53/0438 |
| 2019/0204008 A1 | * | 7/2019 | Van Willigenburg | F25J 3/0242 |
| 2020/0109893 A1 | * | 4/2020 | Ducote, Jr. | F25J 3/0655 |
| 2020/0165177 A1 | * | 5/2020 | Höfel | C07C 7/09 |
| 2020/0181044 A1 | * | 6/2020 | Höfel | C07C 5/333 |
| 2021/0070676 A1 | * | 3/2021 | Reyneke | C07C 7/04 |
| 2021/0094895 A1 | * | 4/2021 | Tuat Pham | C07C 7/005 |
| 2021/0130263 A1 | * | 5/2021 | Jo | C07C 7/09 |

\* cited by examiner

*Primary Examiner* — Tam M Nguyen
(74) *Attorney, Agent, or Firm* — Gary M. Machetta

(57) ABSTRACT

In a propane dehydrogenation (PDH) process, the purpose of the deethanizer and chilling train systems is to separate the cracked gas into a methane-rich tail gas product, a C2, and a C3 process stream. By the use of staged cooling, process-to-process inter-change against propane feed to the reactor and use of high efficiency heat exchangers and distributed distillation techniques, refrigeration power requirements are reduced and a simple and reliable design is provided by the process described herein.

4 Claims, 1 Drawing Sheet

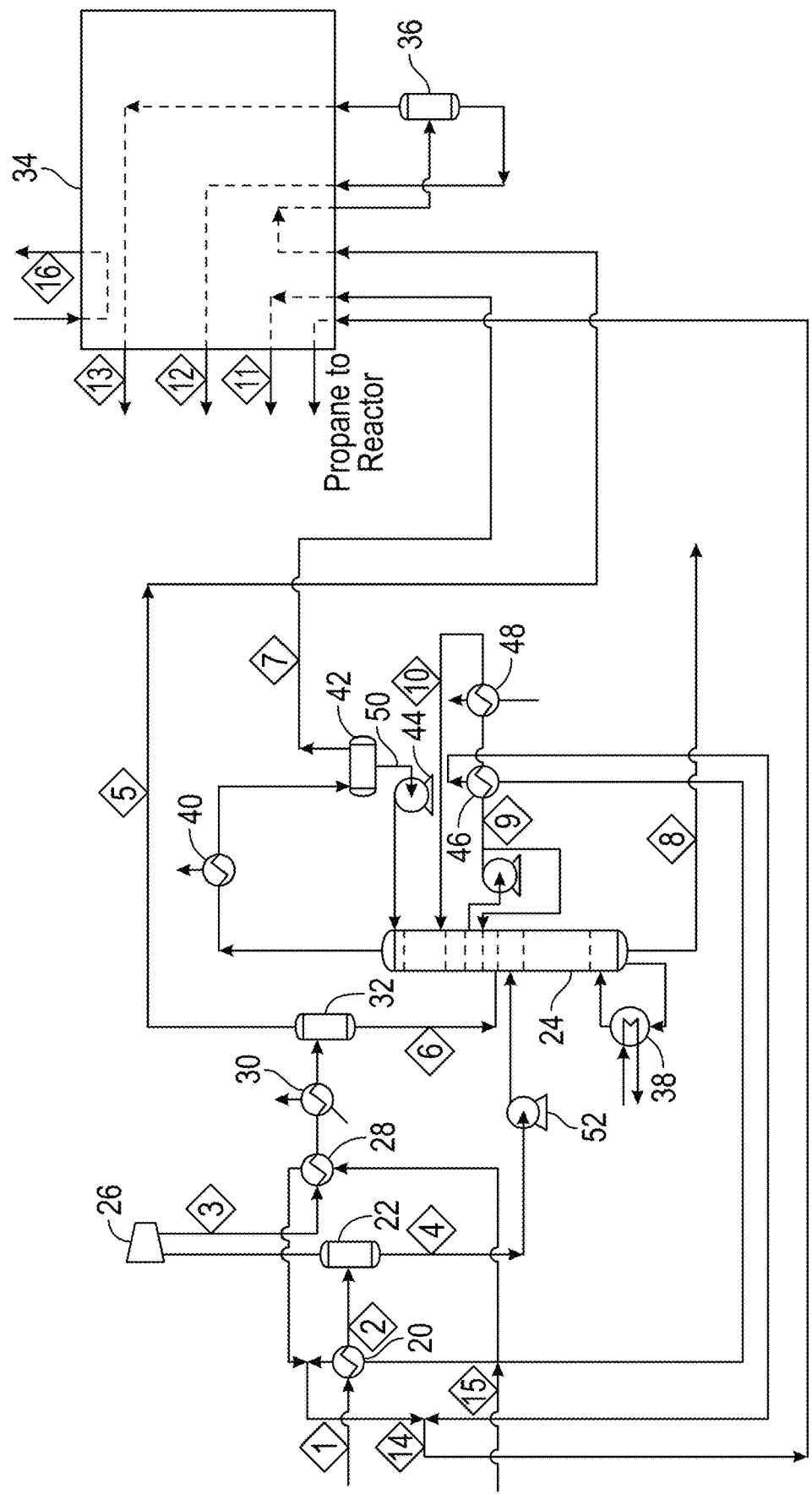

SYSTEM FOR RECOVERY OF PROPYLENE FROM A PROPANE DEHYDROGENATION PROCESS

CROSS-REFERENCES TO RELATED APPLICATIONS

This application is a divisional application from U.S. patent application Ser. No. 17/016,512 filed Sep. 10, 2020, now U.S. Pat. No. 11,198,661, which in turn claims the benefit of U.S. Provisional Patent Application Ser. No. 62/898,426 filed Sep. 10, 2019, both of which are incorporated herein by reference in their entirety.

TECHNICAL FIELD

The present invention relates to a process for recovering propylene from a propane dehydrogenation (PDH) process, and more particularly relates to recovering a methane-rich, C2-rich and C3-rich product from a PDH process.

BACKGROUND

Propane dehydrogenation (PDH) is a process step in the production of propylene from propane. PDH is important to the petrochemical industry because propylene is the second most important starting product in the petrochemical industry after ethylene. The purpose of a deethanizer and chilling train systems in a PDH process is to separate the cracked gas into a methane-rich tail gas product, a C2 process stream and a C3 process stream. It would always be beneficial to improve a PDH process, such as by reducing refrigeration power requirements, simplifying the design, and/or making the design more reliable.

BRIEF DESCRIPTION OF THE DRAWINGS

FIG. 1 is a non-limiting, schematic illustration of a PDH process as described herein.

SUMMARY

There is provided, in one non-limiting embodiment a process for recovering propylene from a propane dehydrogenation (PDH) process comprising a PDH Reactor, where the process includes feeding dried process gas from a Process Gas Dryer to a First Deethanizer Feed Chiller and chilling it against propane; sending the chilled dried process gas to a First Deethanizer Feed Drum; feeding liquid from First Deethanizer Feed Drum to a Deethanizer; sending the overhead vapors from the First Deethanizer Feed Drum to a Process Gas Compressor (PGC); cooling the discharge from the PGC against propane in a Second Deethanizer Feed Chiller, followed by propylene refrigerant in a Third Deethanizer Feed Chiller, and send discharge to a Second Deethanizer Feed Drum; feeding liquid from Second Deethanizer Feed Drum to the Deethanizer; chilling and partially condensing the vapor from the Second Deethanizer Feed Drum in a Cold Box; separating process effluent from the Cold Box into vapor and liquid phases in a First Cold Drum; vaporizing liquid from the First Cold Drum in the Cold Box and recycling it to a first stage of the PGC; reheating the vapor from First Cold Drum to become a methane-rich tail gas product; separating ethane and lighter components from C3 and heavier components in the Deethanizer; reboiling deethanizer bottoms liquid against quench water or propylene refrigerant vapor in a Deethanizer Reboiler and partially condensing overhead vapor against Propylene refrigerant in a Deethanizer Condenser; separating process effluent from the Deethanizer Condenser into vapor and liquid phases in a Deethanizer Reflux Drum and sending a vapor phase to Cold Box and returning the liquid back to the deethanizer; withdrawing a liquid stream from above the upper feed stage of the Deethanizer, pumping and then optionally cooling it in a First Pumparound cooler against propane followed by propylene refrigerant in a Second Pumparound cooler, and returning the cooled liquid to the Deethanizer at a location higher than the draw tray; feeding Deethanizer bottoms liquid to a C3 Splitter; and the Cold Box superheating tail gas from First Cold Drum, a PGC Recycle stream, a C2 Rich Stream, and Propane feed to the PDH Reactor while also subcooling liquid propylene refrigerant.

There is additionally provided in one non-restrictive version, a system for recovering propylene from a propane dehydrogenation (PDH) process comprising a PDH Reactor, where the system includes a Process Gas Dryer configured to feed dried process gas to a First Deethanizer Feed Chiller and chill it against propane; a First Deethanizer Feed Drum configured to receive the dried process gas from the First Deethanizer Feed Chiller; a Deethanizer configured to receive liquid from the First Deethanizer Feed Drum; a Process Gas Compressor (PGC) configured to receive overhead vapors from the First Deethanizer Feed Drum; a Second Deethanizer Feed Chiller configured to cool discharge from the PGC against propane; a Third Deethanizer Feed Chiller configured to cool discharge from the PGC with propylene refrigerant; a Second Deethanizer Feed Drum configured to receive discharge from the Third Deethanizer Feed Chiller and to send feed liquid to the Deethanizer; a Cold Box configured to receive, chill, and partially condense vapor from the Second Deethanizer Feed Drum; a First Cold Drum configured to separate process effluent from the Cold Box into vapor and liquid phases and recycling vaporized liquid to a first stage of the PGC; an overhead Deethanizer Condenser configured to partially condense overhead vapor against Propylene refrigerant; a Deethanizer Reflux Drum configured to separate process effluent from the overhead Deethanizer Condenser into vapor and liquid, sending a vapor phase to the Cold Box; a line directing the liquid from the Deethanizer Reflux Drum to the Deethanizer; and a C3 Splitter configured to receive bottoms liquid from the Deethanizer. Optionally, the system may additionally include a Deethanizer Reboiler configured to reboil deethanizer bottoms liquid against propylene refrigerant vapor.

DETAILED DESCRIPTION

It has been discovered that refrigeration power requirements are reduced and a simple and reliable design is provided for a propane dehydrogenation (PDH) process by the use of staged cooling, process-to-process inter-change against propane feed to the reactor and the use of high efficiency heat exchangers and distributed distillation techniques.

In more detail, and with reference to FIG. 1, which when viewed together are a complete but non-limiting schematic illustration of the process described herein, dried process gas and liquid are fed to the Deethanizer system. More specifically, dry process gas 1 from the Process Gas Dryer (not shown—coming from the left of FIG. 1) is chilled against Propane, from Propane Inlet Stream 15, in First Deethanizer Feed Chiller 20 and sent to the First Deethanizer Feed Drum 22 as gas 2. Liquid 4 from First Deethanizer Feed Drum 22 is fed to Deethanizer Column 24, in one non-restrictive version by pumping with Condensate Pump 52. The overhead vapors go to third stage Process Gas Compressor (PGC) 26. The discharge 3 from Process Gas Compressor 26 is cooled against propane, also from Propane Inlet Stream 15, in Second Deethanizer Feed Chiller 28, followed by propylene refrigerant in Third Deethanizer Feed Chiller 30 and sent to Second Deethanizer Feed Drum No. 2 (V-4002). Liquid 6 from Second Deethanizer Feed Drum No. 2 (V-4002) 32 is fed to Deethanizer Column 24. Propane 14 from Second Deethanizer Feed Chiller 28 is routed to Cold Box 34 prior to being fed to the PDH Reactor.

The vapor 5 from Second Deethanizer Feed Drum 32 is chilled and partially condensed in Cold Box 34. The process effluent from Cold Box 34 is separated into vapor and liquid phases in First Cold Drum 36. The liquid 12 from First Cold Drum 36 is vaporized in Cold Box 34 and recycled to PGC first stage to recover the contained propylene. The vapor from First Cold Drum 36 is reheated and becomes a methane-rich tail gas product 13.

Deethanizer Column 24 separates ethane and lighter components from the C3 and heavier components. The deethanizer bottoms liquid is reboiled against quench water or propylene refrigerant vapor in Deethanizer Reboiler 38. The overhead vapor is partially condensed against Propylene refrigerant in Deethanizer Condenser 40. The Deethanizer Condenser 40 process effluent is separated into vapor and liquid phases in Deethanizer Reflux Drum 42. The vapor phase 7 goes to Cold Box 34. The liquid is directed back to the Deethanizer Column 24, optionally pumped by Deethanizer Reflux Pump 44. The Deethanizer bottoms liquid proceeds to the C3 Splitter as feed.

A pumparound 9 on the Deethanizer 24 upper section is cooled against propane, from Propane Inlet Stream 15, in Deethanizer First Pumparound Cooler 46 and mid-level propylene refrigerant in Deethanizer Second Pumparound Cooler 48 and the cooled stream 10 is returned to the Deethanizer Column 24 at a higher tray location to reduce the requirement for low-level refrigerant on the overhead Deethanizer Condenser 40.

Cold Box 34 superheats tail gas from First Cold Drum 36, PGC Recycle stream 12, C2 Rich Stream 11, and Propane to Reactor while subcooling Liquid Propylene Refrigerant 16.

The Deethanizer bottoms stream 8 feed to a heat-pumped C3 Splitter where polymer-grade propylene is separated from the propane recycle and C4+ components. In one non-limiting embodiment, the majority of propane recycle is taken as a side draw from the C3 Splitter, which bypasses the Depropanizer, while the remaining C3 recycle and C4+ material is recycled to the Depropanizer column (not shown), where C4+ is separated from fresh feed and recycle propane.

In one non-limiting embodiment, the operating condition ranges for certain equipment of the method may be as given in Table I:

TABLE I

Operating Conditions for Recovery of Propylene in a PDH Process

| Name | Temperature | Pressure |
|---|---|---|
| 1st Deethanizer Feed Drum 22 | 10° C. to −5° C. | 10-15 barg |
| 2nd Deethanizer Feed Drum 32 | −25° C. to −40° C. | 20-40 barg |
| Deethanizer Column 24 | −40° C. (top) to +40° C. bottom | 10-15 barg |
| Deethanizer Reflux Drum 42 | −30° C. to −40° C. | 10-15 barg |
| First Cold Drum 36 | −40° C. to −100° C. | 20-40 barg |
| Cold Box 34 | −120° C. to +40° C. | |

The process for recovering propylene from a PDH process as described herein has a number of advantages including but not limited to, reduced power requirements, high propylene recovery, a simpler design, and increased reliability. In one non-limiting embodiment, using liquid propane feed to the reactor to first provide refrigeration to the process results in power savings in the range of about 30% to 50% compared to a design where the depropanizer overhead is produced as a vapor and feeds directly to the reactor. The design uses only a propylene refrigeration system for simplicity, but still achieves good propylene recovery by recycling the liquid produced in First Cold Drum No. 1 and using it as cooling medium in the cold box.

In the foregoing specification, the invention has been described with reference to specific embodiments thereof. However, the specification is to be regarded in an illustrative rather than a restrictive sense. For example, equipment, processes, and operating conditions falling within the claimed or disclosed parame-ters, but not specifically identified or tried in a particular example, are expected to be within the scope of this invention.

The present invention may be practiced in the absence of an element not disclosed. In addition, the present invention may suitably comprise, consist or consist essentially of the elements disclosed. For instance, there may be provided a process for recovering propylene from a PDH process that comprises a PDH Reactor, where the process further consists essentially of or consists of:

feeding dried process gas from a Process Gas Dryer to a First Deethanizer Feed Chiller and chilling it against propane;

sending the chilled dried process gas to a First Deethanizer Feed Drum;

feeding liquid from First Deethanizer Feed Drum to a Deethanizer;

sending the overhead vapors from the First Deethanizer Feed Drum to a Process Gas Compressor (PGC);

cooling the discharge from the PGC against propane in a Second Deethanizer Feed Chiller, followed by propylene refrigerant in a Third Deethanizer Feed Chiller, and sending the discharge to a Second Deethanizer Feed Drum;

feeding liquid from Second Deethanizer Feed Drum to a Deethanizer;

chilling and partially condensing the vapor from the Second Deethanizer Feed Drum in a Cold Box;

separating process effluent from the Cold Box into vapor and liquid phases in a First Cold Drum;

vaporizing liquid from the First Cold Drum in the Cold Box and recycling it to a first stage of the PGC;

reheating the vapor from First Cold Drum to become a methane-rich tail gas product;

separating ethane and lighter components from C3 and heavier components in the Deethanizer;

reboiling deethanizer bottoms liquid against quench water or propylene refrigerant vapor in a Deethanizer Reboiler and partially condensing overhead vapor against Propylene refrigerant in a Deethanizer Condenser;

separating process effluent from the Deethanizer Condenser into vapor and liquid phases in a Deethanizer Reflux Drum and sending a vapor phase to Cold Box and returning the liquid back to the deethanizer, optionally by a Deethanizer Reflux Pump;

withdrawing a liquid stream from above the upper feed stage of the Deethanizer, pumping and then cooling it in a First Pumparound cooler against propane followed by propylene refrigerant in a Second Pumparound cooler, and returning the cooled liquid to the Deethanizer at a location higher than the draw tray;

feeding Deethanizer bottoms liquid to a C3 Splitter; and the Cold Box superheating tail gas from First Cold Drum, a PGC Recycle stream, a C2 Rich Stream, and Propane feed to the PDH Reactor while also subcooling liquid propylene refrigerant.

Alternatively there may be provided a system for recovering propylene from a propane dehydrogenation (PDH) process comprising a PDH Reactor, where the system consists essentially of or consists of:

a Process Gas Dryer configured to feed dried process gas to a First Deethanizer Feed Chiller and chill it against propane;

a First Deethanizer Feed Drum configured to receive the dried process gas from the First Deethanizer Feed Chiller;

a Deethanizer configured to receive liquid from the First Deethanizer Feed Drum;

a Process Gas Compressor (PGC) configured to receive overhead vapors from the First Deethanizer Feed Drum;

a Second Deethanizer Feed Chiller configured to cool discharge from the PGC against propane;

a Third Deethanizer Feed Chiller configured to cool discharge from the PGC with propylene refrigerant;

a Second Deethanizer Feed Drum configured to receive discharge from the Third Deethanizer Feed Chiller and to send feed liquid to the Deethanizer;

a Cold Box configured to receive, chill, and partially condense vapor from the Second Deethanizer Feed Drum;

a First Cold Drum configured to separate process effluent from the Cold Box into vapor and liquid phases and recycling vaporized liquid to a first stage of the PGC;

an overhead Deethanizer Condenser configured to partially condense overhead vapor against Propylene refrigerant;

a Deethanizer Reflux Drum configured to separate process effluent from the overhead Deethanizer Condenser into vapor and liquid, sending a vapor phase to the Cold Box;

a line directing the liquid from the Deethanizer Reflux Drum to the Deethanizer; and a C3 Splitter configured to receive bottoms liquid from the Deethanizer.

In another non-limiting, alternate embodiment, the system may additionally consist essentially of or consist of a Deethanizer Reboiler configured to reboil deethanizer bottoms liquid against propylene refrigerant vapor.

The words "comprising" and "comprises" as used throughout the claims, are to be interpreted to mean "including but not limited to" and "includes but not limited to", respectively.

As used herein, the word "substantially" shall mean "being largely but not wholly that which is specified."

As used herein, the singular forms "a," "an," and "the" are intended to include the plural forms as well, unless the context clearly indicates otherwise.

As used herein, the term "about" in reference to a given parameter is inclusive of the stated value and has the meaning dictated by the context (e.g., it includes the degree of error associated with measurement of the given parameter).

As used herein, the term "and/or" includes any and all combinations of one or more of the associated listed items.

The invention claimed is:

1. A system for recovering propylene from a propane dehydrogenation (PDH) process comprising a PDH Reactor, the system comprising:

a Process Gas Dryer configured to feed dried process gas to a First Deethanizer Feed Chiller and chill it against propane;

a First Deethanizer Feed Drum configured to receive the dried process gas from the First Deethanizer Feed Chiller;

a Deethanizer configured to receive liquid from the First Deethanizer Feed Drum;

a Process Gas Compressor (PGC) configured to receive overhead vapors from the First Deethanizer Feed Drum;

a Second Deethanizer Feed Chiller configured to cool discharge from the PGC against propane;

a Third Deethanizer Feed Chiller configured to cool discharge from the PGC with propylene refrigerant;

a Second Deethanizer Feed Drum configured to receive discharge from the Third Deethanizer Feed Chiller and to send feed liquid to the Deethanizer;

a Cold Box configured to receive, chill, and partially condense vapor from the Second Deethanizer Feed Drum;

a First Cold Drum configured to separate process effluent from the Cold Box into vapor and liquid phases and recycling vaporized liquid to a first stage of the PGC;

an overhead Deethanizer Condenser configured to partially condense overhead vapor against Propylene refrigerant;

a Deethanizer Reflux Drum configured to separate process effluent from the overhead Deethanizer Condenser into vapor and liquid, sending a vapor phase to the Cold Box;

a line directing the liquid from the Deethanizer Reflux Drum to the Deethanizer; and a C3 Splitter configured to receive bottoms liquid from the Deethanizer.

2. The system of claim 1 further comprising a Deethanizer Reboiler configured to reboil deethanizer bottoms liquid against propylene refrigerant vapor.

3. The system of claim 1 further comprising a Deethanizer Reboiler configured to reboil deethanizer bottoms liquid against quench water.

4. The system of claim 1 further comprising a pumparound on an upper section of the Deethanizer, which pumparound uses propane in a Deethanizer First Pumparound Cooler and mid-level propylene refrigerant in a Deethanizer Second Pumparound Cooler.

* * * * *